(12) United States Patent
Wagner et al.

(10) Patent No.: US 9,243,991 B2
(45) Date of Patent: Jan. 26, 2016

(54) DEVICE AND PROCESS FOR TESTING HOLLOW FIBRE MEMBRANE FILTERS

(75) Inventors: Steffen Wagner, Messstetten (DE); Philipp Herbst, Mossingen (DE); Bernd Krause, Rangendingen (DE)

(73) Assignee: Gambro Lundia AB, Lund (SE)

( * ) Notice: Subject to any disclaimer, the term of this patent is extended or adjusted under 35 U.S.C. 154(b) by 362 days.

(21) Appl. No.: 13/814,125

(22) PCT Filed: Aug. 10, 2011

(86) PCT No.: PCT/EP2011/063756
§ 371 (c)(1),
(2), (4) Date: Feb. 20, 2013

(87) PCT Pub. No.: WO2012/020048
PCT Pub. Date: Feb. 16, 2012

(65) Prior Publication Data
US 2013/0205873 A1 Aug. 15, 2013

(30) Foreign Application Priority Data

Aug. 11, 2010 (EP) ..................................... 10172450

(51) Int. Cl.
*G01N 15/08* (2006.01)
*B01D 65/10* (2006.01)

(52) U.S. Cl.
CPC ............ *G01N 15/082* (2013.01); *B01D 65/102* (2013.01); *B01D 2313/10* (2013.01); *G01N 15/0826* (2013.01); *G01N 2015/084* (2013.01)

(58) Field of Classification Search
CPC ........................ G01N 2015/084; G01N 15/082
USPC ............... 73/37, 38, 861.42; 210/87, 90, 646, 210/650, 652
See application file for complete search history.

(56) References Cited

U.S. PATENT DOCUMENTS

| | | | | |
|---|---|---|---|---|
| 4,614,109 | A | | 9/1986 | Hofmann et al. |
| 4,702,829 | A | * | 10/1987 | Polaschegg ......... A61M 1/3413 210/195.2 |
| 5,064,529 | A | * | 11/1991 | Hirayama ............... A61L 2/022 210/140 |
| 5,507,959 | A | * | 4/1996 | Glick ................... B01D 65/102 210/136 |
| 5,594,161 | A | * | 1/1997 | Randhahn ............ B01D 29/114 73/38 |
| 5,808,181 | A | * | 9/1998 | Wamsiedler ........ A61M 1/3455 210/646 |
| 6,228,271 | B1 | * | 5/2001 | Cote .................... B01D 65/105 210/739 |
| 6,568,282 | B1 | * | 5/2003 | Ganzi .................. B01D 65/102 73/38 |
| 2009/0057225 | A1 | * | 3/2009 | Krause ............... B01D 67/0011 210/650 |

FOREIGN PATENT DOCUMENTS

| | | |
|---|---|---|
| EP | 0407737 | 6/1990 |
| EP | 0592066 | 4/1993 |
| EP | 1898973 | 3/2008 |
| JP | 10015059 | 1/1998 |
| JP | 2004167384 | 6/2004 |
| WO | WO2007/003980 | 1/2007 |

OTHER PUBLICATIONS

PCT Search Report and Written Opinion for PCT/EP2011/063756, completed May 12, 2011.

* cited by examiner

*Primary Examiner* — Hezron E Williams
*Assistant Examiner* — Hoang Nguyen
(74) *Attorney, Agent, or Firm* — Barnes & Thornburg LLP

(57) ABSTRACT

A process and a device for testing a hollow fiber membrane filter comprises two compartments separated by a porous membrane. A specific amount of testing liquid is provided via a line from a testing liquid reservoir.

16 Claims, 1 Drawing Sheet

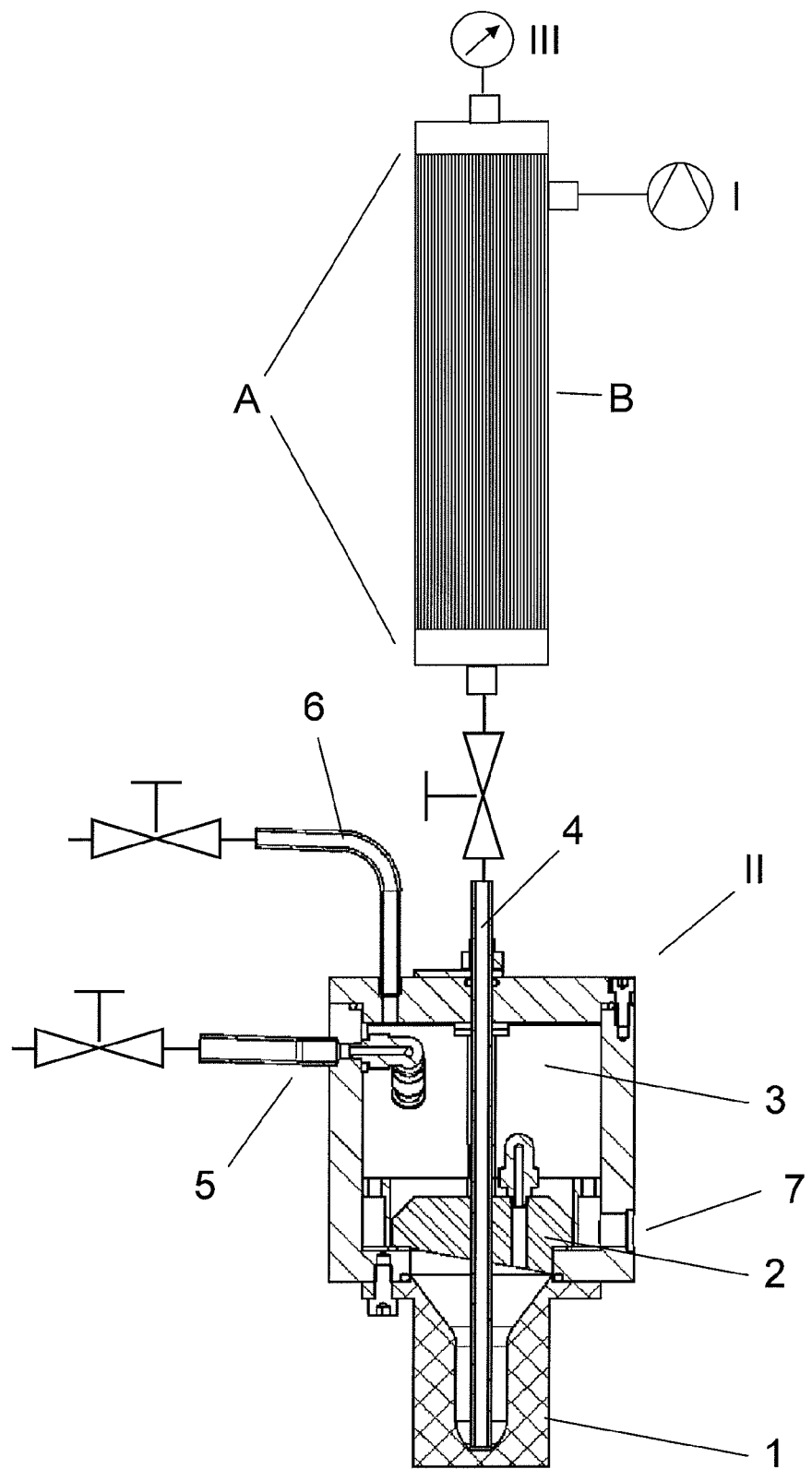

DEVICE AND PROCESS FOR TESTING HOLLOW FIBRE MEMBRANE FILTERS

CROSS-REFERENCE TO RELATED APPLICATIONS

This application is the U.S. national phase of PCT/EP2011/063756 filed Aug. 10, 2011. PCT/EP2011/063756 claims benefit under the Convention to EP 10172450.8 filed Aug. 11, 2010. The disclosures of EP 10172450.8 and PCT/EP2011/063756 are hereby incorporated herein by reference.

TECHNICAL FIELD

The present disclosure relates to a device and a process for testing filters. Specifically, though not exclusively, the invention can be usefully applied for filters of an apparatus for extracorporeal blood treatment, for instance, membrane filters normally used in a device for on-line preparation of a dialysis liquid and/or a replacement liquid, in the ambit of an apparatus for hemodialysis and/or hemo(dia)filtration, or filters used for hemodialysis and/or hemo(dia)filtration.

DESCRIPTION OF THE RELATED ART

Diffusion and/or filtration devices comprising hollow fiber membranes are used in various medical treatments which remove unwanted substances from body fluids, e.g., blood. Examples of such treatments are hemodialysis, hemodiafiltration and hemofiltration. Membrane filters are also used in the production of sterile liquids, by causing the liquid to pass through a semi-permeable membrane able to filter the germs. Various processes for checking the integrity of a filter have been described.

One of the known processes is the bubble point test (BPT), which can check on the absence of membrane pores which have a greater size than a predetermined limit. The BPT considers the membrane pores as capillary tubes, and the maximum radius of the pores is determined by pressure measurements. The test briefly comprises the following stages: the membrane is wetted so that the pores are full of liquid; a first side of the membrane is connected to a gas source, while the opposite side is connected to a liquid for easy detection of gas bubbles; the first side of the membrane is gradually pressurized with the gas; while the gas pressure on the first side remains relatively low, a modest amount of gas will displace, by diffusion, through the liquid contained in the membrane pores towards the second side of the membrane; this amount of gas flow is proportional to the speed of increase of gas pressure on the first side; when the gas pressure reaches a certain level, the liquid contained in the largest pores is forced to exit from the pores themselves, and a considerable amount of gas crosses the largest pores, reaching the liquid connected to the second side of the membrane, forming gas bubbles within the liquid; in this situation a further pressuring action leads to a further displacement of gas towards the second side of the membrane, with no discernible increase in pressure; the substantially stable pressure reached in this situation (bubble point pressure, or BP pressure) is a known function of the maximum radius of the membrane pores and thus enables determination thereof; stopping the pressurization action leads to a situation of substantial equilibrium in the BP pressure.

U.S. Pat. No. 5,064,529 describes an automatic BPT (without the need to observe the moment of gas bubble formation) to check whether the effective BP pressure of the membrane corresponds to the desired BP pressure corresponding to the maximum diameter of the pores indicated by the membrane manufacturer; in a first stage the first side of the membrane is pressurized with the gas at a predetermined constant pressurization speed, at the end of which first stage the pressure measured on the first side of the membrane should correspond to a predetermined theoretical pressure; the pressurization speed and the pressurization time are chosen so that the above-mentioned theoretical pressure is lower than the desired BP pressure; if the pressure measured after the predetermined time does not correspond to the theoretical pressure, a fault is signaled due, probably, to the breakage of the membrane or a faulty installation of the filter; in a second stage, the pressurization is halted for a certain time period in which the pressure should remain substantially constant; if, on the contrary, there is a significant drop in pressure, a fault is signaled due, probably, to the faulty filling-up of the pores with the liquid; in a third stage, the pressurization of the first side of the membrane is re-established at a predetermined speed for a predetermined time, during which theoretically the desired BP pressure is reached; if, at the end of the third stage, the desired BP pressure is measured, within a predetermined range of acceptability, it is considered that the maximum diameter of the pores is the desired one.

U.S. Pat. No. 5,594,161 describes a process for testing the integrity of one or more filtering elements in which the inlet side of the filter element is wetted and subjected to a gas pressure which is kept constant, while the pressure is measured on the outlet side which, previously, has been made part of a closed system. If, after a predetermined time, the outlet pressure does not exceed a predetermined threshold value, the filter element is considered intact.

U.S. Pat. No. 4,614,109 describes a process for checking the permeability of a wet membrane of a filter, based both on a search for the BP pressure and on the determination of the gas diffusion before reaching BP pressure. In this process, the filter membrane is first impregnated with liquid; thereafter, the inlet side of the membrane is gradually pressurized by introduction of a gas; the gas that passes by diffusion through the membrane is collected in a graduated container; the permeability of the membrane is calculated on the basis of the trans-membrane pressure measured on the two sides of the membrane, and of the quantity of gas diffused through the membrane per unit of time using the graduated container. By continuing with the pressurization, at a certain point (called the visual bubble point because it can be visually detected) the production of gas bubbles on the exit side of the membrane sharply increases: this, as mentioned above, is due to the fact that, on reaching the bubble point pressure, the passage of gas through the membrane occurs both by diffusion (in a small part) and (prevalently) by effect of the formation of gas conduits through the pores of the membrane.

U.S. Pat. No. 6,228,271 describes a process for testing the integrity of filter membranes in which the filter inlet chamber is emptied of liquid and filled with air at atmospheric pressure, while the outlet chamber remains full of liquid. A depression is then created in the outlet chamber in order to create a trans-membrane pressure; after the depression has been stabilized, for example at a value comprised between 0.2 and 0.9 bar (absolute pressure), and before completely evacuating the liquid from the outlet chamber, the constant flow of liquid is measured as it exits the outlet chamber, which corresponds to the air flow passing through the perforations of the membrane; the integrity of the membrane is thus measured on the basis of the value measured for the liquid flow.

Another known process for measuring the integrity of a filter membrane involves verification under sealed pressure, where a trans-membrane pressure gradient is created and monitored over time in at least one chamber of the filter. A typical sealed pressure test involves, for example, a side of the membrane being brought up to a predetermined gas pressure, below BP pressure, comprised in the diffusion range, i.e. a range in which the pressure in the second membrane chamber increases proportionally to the pressure in the first side; when the pressure has been reached, the gas supply is interrupted and the pressure on the first side monitored; if the drop in pressure per time unit exceeds a predetermined threshold value, the membrane is understood to exhibit some defects.

U.S. Pat. No. 4,702,829 describes a process, of the pressurized sealed type, for verifying the integrity of the filters of a hemodiafiltration apparatus, in which the substitution liquid is realized on-line by passing the dialyzer liquid through two sterile filters arranged one after another, each of which exhibits two chambers separated by a water-wettable and semi-permeable membrane, which can hold the germs. The verification process of the filter seal begins after the dialysis circuit washing stage, with the circuit full of the detergent liquid and the water-wettable filter membranes wet. The filter seal verification process uses an ultrafiltration pump, predisposed in the dialysis circuit downstream of the blood treatment device and used in the dialysis treatment for obtaining a patient weight drop measurement. During the filter test, the ultrafiltration pump is used to aspirate air internally of the first chamber of the second filter, through a micro-porous water-repelling filter arranged in a breather of the first chamber. The aspirated air can also enter the second chamber of the first filter in the absence of occlusions in the circuit branch comprised between the two filters. The liquid that leaves space for the aspirated air is removed by the ultrafiltration pump through the membranes of the two filters. Given that the water-wettable membranes of the filters are wet, the membranes themselves are substantially impermeable to air. Therefore, once the second chamber of the first filter and the first chamber of the second filter are entirely occupied by air at atmospheric pressure, and since the air that has entered the chambers cannot escape through the membrane, the ultrafiltration pump can generate a depression in chambers occupied by the liquid, i.e. the first chamber of the first filter and the second chamber of the second filter. The ultrafiltration pump is then activated until a determined depression has been reached in a part of the dialysis circuit filled with liquid. Thereafter, the depression is monitored using a pressure gauge, for example by measuring the time necessary for the pressure to rise by a predetermined quantity, or by measuring the depression after a determined period of time. The monitoring of the depression enables an evaluation of the fluid seal of the system constituted by the membranes and the part of the circuit under depression.

U.S. Pat. No. 5,808,181 describes a process for verifying membrane filters arranged in the dialysis circuit of a device for extracorporeal blood treatment, in which the membrane of a filter to be checked is completely wetted with a liquid, a branch of the dialysis circuit containing one of the two filter chambers to be verified is separated from the rest of the circuit, a gas is injected into the separated branch to cause an overpressure, while the liquid contained in the chamber is removed by passing through the membrane; the gas supply is interrupted after a predetermined overpressure level has been reached in chamber; thereafter, the overpressure is controlled, for example by comparing the pressure drop per time unit with a limit value which is characteristic of an intact filter membrane.

EP-A 0 407 737 describes a process for testing the membrane of a dialyzer filter in two stages: in a first stage the blood chamber of the dialyzer is subjected to a pressure gradient from the blood chamber to the dialyzer fluid chamber; in a second stage the membrane is subjected to an opposite gradient. The test enables a determination of the presence of leaks which might appear or be noted only by effect of one or other of the two pressure gradients.

EP-A 1 898 973 discloses a process for testing filters of treatment fluid of a hemodiafiltration apparatus, wherein each filter has a wet semipermeable membrane which separates a gas-filled first chamber from a liquid-filled second chamber. The first chambers are pressurized by a pump supplying air, while the second chambers are placed in depression by a drainage pump of used dialysis fluid. A first closed system is formed which includes the first chambers and a second closed system is formed which includes the second chambers. Two pressure gauges monitor the pressure in the two closed systems for a predetermined time.

SUMMARY

A principal aim of the present invention is to provide a reliable and fast process for the testing of filters comprising two compartments separated by a porous membrane. A further aim of the invention is to provide an apparatus for actuating the process.

The process of the invention involves establishing a pressure gradient between the compartments of the dry filter, introducing a predefined volume of a testing liquid, e.g. water, into the compartment having the higher pressure, allowing the testing liquid to wet the porous membrane, and subsequently monitoring the pressure gradient between the compartments or measuring gas flow through the membrane.

The testing apparatus of the invention comprises means for establishing a pressure gradient between the compartments of the filter, means for introducing a predefined quantity of a testing liquid, e.g. water, into the filter and means for monitoring pressure in the filter.

Further characteristics and advantages of the present invention will better emerge from the detailed description that follows of at least a preferred embodiment of the invention, illustrated purely in the form of a non-limiting example in the accompanying FIGURES of the drawings.

BRIEF DESCRIPTION OF THE DRAWINGS

FIG. 1 is a sectional view of an exemplary embodiment of the testing apparatus of the invention.

DETAILED DESCRIPTION

The present invention provides a process for testing a filter comprising two compartments separated by a porous membrane, comprising
  i) providing a filter having a dry porous membrane;
  ii) establishing a pressure gradient between the compartments;
  iii) introducing a volume of testing liquid which is sufficient to substantially reduce gas permeability of the porous membrane but is less than or equal to the total pore volume of the porous membrane into the compartment having the higher pressure and allowing the testing liquid to wet the porous membrane;
  iv) monitoring the pressure gradient between the compartments or measuring gas flow through the membrane.

The process of the invention is suitable for testing the integrity of filters comprising two compartments separated by a porous membrane. Examples of such filters are membrane filters used in extracorporeal blood treatment, e.g. dialyzers;

filters used in the preparation of medical fluids, e.g., pyrogen-free and germ-free fluids like dialysis fluid or substitution fluid; virus filters; blood oxygenators; and reverse osmosis filters.

Each one of the two compartments of the filter generally has at least one fluid inlet or outlet, respectively. In one embodiment, each of the two compartments has one fluid inlet and one fluid outlet. In another embodiment, only one of the compartments has both a fluid inlet and a fluid outlet, while the other compartment only has a fluid inlet. In still another embodiment, only one of the compartments has both a fluid inlet and a fluid outlet, while the other compartment only has a fluid outlet. In still another embodiment, only one of the compartments only has a fluid inlet, while the other compartment only has a fluid outlet.

The dry porous membrane of the filter may take different forms. In one embodiment, the membrane is a flat sheet membrane or a stack of flat sheet membranes. In another embodiment, the porous membrane is a hollow fiber membrane or a bundle of hollow fiber membranes.

The porous membrane may be hydrophilic or hydrophobic, and is comprised of inorganic materials like carbon, glass, ceramics or metals, or organic materials like synthetic polymers. Examples of suitable synthetic polymers comprise hydrophobic polymers like polysulfones, polyethersulfones, polytetrafluoroethylene, polyvinylidene fluoride, polypropylene and hydrophilic polymers like polyvinyl pyrrolidone (PVP), polyethylene glycol (PEG), or EVA.

The testing liquid is a liquid which is able to wet the membrane surface and fill the pores of the membrane. Suitable testing liquids are chosen according to the properties of the membrane. For hydrophilic membranes, water, methanol, ethanol or mixtures thereof can be used as testing liquid. In one embodiment of the invention, water is used as testing liquid. For hydrophobic membranes, isopropanol is a suitable testing liquid. Other suitable testing liquids for hydrophobic membranes include liquid hydrocarbons or silicone oils.

At the beginning of the process of the invention, the porous membrane in the filter is dry. A pressure gradient is established between the compartments and a predefined volume of testing liquid is introduced into the compartment of the filter having the higher pressure, so that the testing liquid is forced into the membrane. It is a characteristic feature of the process of the invention that instead of flooding the filter with testing liquid, only a limited volume of testing liquid is introduced into the filter, the volume being sufficient to wet the membrane surface and to substantially reduce gas permeability of the porous membrane, but being less than or equal to the total pore volume of the porous membrane.

The total pore volume of the membrane is the portion of the membrane volume which is not occupied by solid material. It can be calculated by subtracting membrane mass divided by the density of the membrane material from the volume of the membrane (wall):

$$V_P = V_M - (m_M/\rho_S),$$

with $V_P$ being the total pore volume of the membrane, $V_M$ being the volume of the membrane (wall), $m_M$ being the mass of the membrane, and $\rho_S$ being the density of the material forming the solid portion of the membrane (wall). Total pore volume divided by the membrane (wall) volume is the porosity P of the membrane: $P = V_P/V_M$.

In one embodiment of the process using a filter comprising a bundle of hollow fiber membranes, the volume of testing liquid introduced into the filter is in the range of from $P \cdot n \cdot L \cdot \pi \cdot (d_i \cdot 20 \ \mu m + 400 \ \mu m^2)$ to $P \cdot n \cdot L \cdot \pi (d_i \cdot w + w^2)$, with n being the number of fibers in the filter, L being the fiber length, P being the porosity of the fiber membrane, $d_i$ being the inner diameter of each fiber, and w being the wall thickness of each fiber.

In one embodiment of the invention, n is in the range of from 1,000 to 20,000. In one embodiment of the invention, L is in the range of from 100 to 350 mm. In one embodiment of the invention, P is in the range of from 0.75 to 0.85, i.e. from 75 to 85%. In one embodiment of the invention, $d_i$ is in the range of from 150 to 350 μm. In one embodiment of the invention, w is in the range of from 20 to 50 μm.

Usually, the volume of testing liquid will be in the range of from 5 to 70 ml.

In one embodiment of the invention, the filter comprises 1,224 fibers having a length L of 122 mm, an inner diameter $d_i$ of 320 μm, a wall thickness w of 50 μm, and a porosity P of 0.78. In one embodiment of the process, the filter is tested using 5 ml of water as testing liquid.

In another embodiment of the invention, the filter comprises 16,800 fibers having a length L of 250 mm, an inner diameter $d_i$ of 190 μm, a wall thickness w of 40 μm, and a porosity P of 0.82. In one embodiment of the process, the filter is tested using 60 ml of water as testing liquid.

In still another embodiment of the invention, the filter comprises 9,612 fibers having a length L of 236 mm, an inner diameter $d_i$ of 190 μm, a wall thickness w of 35 μm, and a porosity P of 0.80. In one embodiment of the process, the filter is tested using 30 ml of water as testing liquid.

In one embodiment of the process, steps ii) and iii) are performed by reducing pressure in the filter by connecting one compartment of the filter to a vacuum line or a vacuum pump, and, subsequently or simultaneously, connecting the other compartment to a testing liquid reservoir containing a predefined volume of testing liquid, so that the testing liquid is sucked into the filter. In another embodiment of the process, the entire filter is evacuated, all inlets/outlets of the filter are closed and one of the inlets is subsequently connected to a testing liquid reservoir containing a predefined volume of testing liquid. In still another embodiment of the process, one compartment of the filter is connected to a pressurized testing liquid reservoir containing a predefined volume of testing liquid, so that the pressure forces the testing liquid into the filter.

The pressure gradient between the compartments carries the testing liquid into the pores of the membrane, filling the pores at least partially. As a result, gas permeability of the membrane is substantially reduced and the membrane becomes largely impermeable to gas, if the membrane is intact. The process is very fast; transfer of testing liquid into the filter and wetting of the membrane is complete within a few seconds.

The magnitude of the pressure gradient is not critical for the process. It will be chosen to be large enough to be within the measuring range of the equipment used for monitoring the pressure gradient between the compartments of the filter or for measuring gas flow through the membrane, respectively. On the other hand, it will be chosen small enough not to compromise mechanical stability of the membrane or the filter.

The pressure gradient between the compartments can then be monitored or the gas flow through the membrane can be measured using methods known in the art, for instance with commercially available leak detectors, to verify the integrity of the filter membrane. In comparison to filters having intact membranes, filters having defective membranes show a faster decrease of the pressure gradient over time between the compartments of the filter, or an increased leak rate.

In one embodiment of the process, a further pressure gradient is established between the compartments of the filter after the membrane has been wetted, i.e. after step iii). For instance, increasing the pressure gradient after the membrane has been wetted may enhance sensitivity or accuracy of the measurement performed in step iv) of the process. It may also be desirable to reverse the pressure gradient between the compartments before the measurement, e.g., to facilitate connection of the measuring equipment to the filter.

In one embodiment of the process, an overpressure is applied to one compartment of the filter after the membrane has been wetted, and the increase of pressure in the other compartment over time is monitored. As an alternative, gas flow through the membrane may be measured. In another embodiment of the process, an overpressure is applied to one compartment of the filter through an inlet of the respective compartment after the membrane has been wetted, the inlet is closed and the decrease of pressure in the compartment over time is monitored.

The process of the invention thus allows for fast and reliable identification of defective filters. It can advantageously be used for quality management in the context of filter production processes. As the process of the invention requires less time than processes known in the art, throughput of the production process can be substantially increased.

In one embodiment of the process, the orientation of the filter during the test is such that the membrane is in a horizontal position. In another embodiment of the process, the orientation of the filter during the test is such that the membrane is in a vertical position. Although the filter can be tested regardless of its orientation, for filters comprising a bundle of hollow fiber membranes, it is preferred that the bundle of hollow fiber membranes is in vertical position during the test.

The predefined amount of testing liquid may be introduced into either compartment of the filter. Of course, pressure conditions within the filter have to be set according to the selection, so that testing liquid is always introduced into the compartment having higher pressure. For filters comprising membranes having a homogeneous structure, e.g., a sponge structure, choice of the compartment is not expected to have substantial impact on the test. If the filter comprises an asymmetric membrane, it is generally preferred to introduce the predefined amount of testing liquid into the compartment bordering the selective side of the membrane, i.e. the membrane surface having the smallest pores. For example, for filters comprising a bundle of asymmetric hollow fiber membranes which have the smallest pores on the inside of the fiber, it is preferred that the predefined amount of testing liquid is introduced into the compartment encompassing the lumen of the hollow fiber membranes.

The present application also provides a device for testing a filter comprising two compartments separated by a porous membrane. The device comprises
  i) means for establishing a pressure gradient between the compartments;
  ii) means for introducing a predefined quantity of testing liquid into the filter;
  iii) means for monitoring pressure in the filter or measuring gas flow through the membrane.

The means for establishing a pressure gradient between the compartments may be a vacuum pump or a vacuum line which is connectable to at least one inlet or outlet of the filter, or a compressor or a pressure line or gas cylinder which is connectable to at least one inlet or outlet of the filter, or a combination thereof.

The means for introducing a predefined quantity of testing liquid into the filter may be any kind of dispensing device capable of dispensing a predefined quantity of testing liquid. Examples include syringes, injection pumps, and metering pumps, e.g., piston-driven metering pumps.

In one embodiment of the device, the means for introducing a predefined quantity of testing liquid into the filter comprise a dosage compartment (1) having an interruptible fluid connection (2) to a testing liquid reservoir (3), an interruptible fluid connection (4) to one of the two compartments of the filter, and a vent pipe (5) comprising a valve.

In a particular embodiment of the device shown in FIG. 1, the means for introducing a predefined quantity of testing liquid into the filter comprise a dosage compartment (1), a moveable lid (2) between the dosage compartment (1) and a testing liquid reservoir (3), a tube (4) forming the connection to the filter, a vent pipe (5) for venting the dosage compartment (1), a vent pipe (6) for venting the testing liquid reservoir (3), and an inlet (7) for supplying testing liquid to the testing liquid reservoir (3). Valves in the tube (4) and the vent pipes (5,6) allow for opening and closing the connections. During operation, the reservoir (3) is filled with testing liquid through inlet (7) while the valve of vent pipe (6) is open. Lid (2) is moved upward while the valves of tube (4) and vent pipe (5) are closed and the testing liquid fills the dosage compartment (1). Lid (2) is lowered to its initial position, sealing the dosage compartment (1). The valves of tube (4) and vent pipe (5) are opened and the testing liquid in dosage compartment (1) is transferred into the filter through tube (4). The dosage compartment (1) is interchangeable with dosage compartments holding differing volumes of testing liquid, so that filters having different sizes of membrane surface area may be tested with the device.

The means for monitoring pressure in the filter or measuring gas flow through the membrane may be any kind of pressure sensors and flow meters that are accurate enough for the device that has to be tested. Examples of such instruments are leak test panels being suitable to detect absolute pressure, difference pressure or mass flow of gas. Such devices are commercially available, for instance, from JW Froehlich GmbH (Leinfelden, Germany) or Zeltwanger Automation GmbH (Dusslingen, Germany). Suitable examples are devices of the MPS series by JW Froehlich, or the DPS-NG series by Zeltwanger Automation GmbH.

It will be understood that the features mentioned above and those described hereinafter can be used not only in the combination specified but also in other combinations or on their own, without departing from the scope of the present invention.

The present invention will now be described in more detail in the examples below. It is to be understood that the examples are not intended to limit the scope of the present invention and are merely an illustration of a preferred embodiment of the invention.

EXAMPLES

Example 1

The integrity of a dry hollow fiber membrane made of polyethersulfone and polyvinylpyrrolidone and mounted in a dialyzer having an inlet and an outlet on both the blood and the dialysate compartment was tested.

The membrane of the dialyzer consisted of 9612 hollow fibers having an inner diameter of 190 µm and a wall thickness of 35 µm, respectively. The fiber length was 260 mm, and the dialyzer provided an effective surface area of 1.35 $m^2$ on the blood-contacting side. The porosity of the membrane was 80%.

Water was used as testing liquid, the volume of water used was 30 ml.

The dialyzer was mounted in a vertical position with the inlet of the blood compartment being directed downwards. The inlet of the blood compartment was connected to the metering device shown in FIG. 1. The outlet of the blood compartment on the opposite side of the dialyzer was closed. The inlet of the dialysate compartment was connected to a vacuum source, the dialyzer being separated from the vacuum source by a valve. The outlet of the dialysate compartment was closed.

The dosage compartment (1) of the metering device is designed to provide a total volume of 30 ml. The reservoir (3) was filled with water through the inlet (7) while the valve of the vent pipe (6) was open. The lid (2) was moved upwards while the valves of the tube (4), which had a diameter of 4 mm and a length of 274 mm, and the vent pipe (5) were closed, and the water filled the dosage compartment (1). The lid (2) was lowered to its initial position sealing the dosage compartment (1).

Simultaneously with the dosage of water into the metering device, vacuum was applied to the dialyzer by opening the valve between the vacuum pump and the dialyzer. As soon as the absolute pressure inside the dialyzer housing reached 100 mbar, the vacuum source was separated from the dialyzer by closing the valve between the vacuum pump and the dialyzer.

After having evacuated the dialyzer, the valves of tube (4) and the vent pipe (5) at the metering device were opened and the water inside the dosage compartment (1) was transferred into the filter through tube (4) by the air stream entering the dosage compartment (1) through the vent pipe (5). Within a few seconds, the water was distributed homogeneously inside the blood compartment, wetting the inner surface of all hollow fiber membranes and thus reducing gas permeability of the porous structure.

In a second step, a leak test panel (Type: MPS200, JW Froehlich GmbH) was connected to the outlet of the blood compartment of the dialyzer. The inlet of the blood compartment remained closed and both ports of the dialysate compartment were opened to atmospheric pressure.

A pressure of 1.6 bar was applied to the blood compartment of the dialyzer for 2.5 seconds, and the ports of the blood compartment were closed. After a leveling phase of one second, pressure decrease inside the blood compartment was measured for another second before the system was vented for 1.5 seconds. The absolute pressure decrease within the measuring phase of one second is an indicator of membrane integrity. Including filling and venting, the total time required for this test was six seconds.

35 pieces of dry dialyzers were processed as described above, 25 pieces having intact membranes and 10 pieces having defective membranes. A mean pressure decrease of 20.1 mbar on the blood contacting side was observed within the measuring phase of one second in case of the 25 dialyzers having intact membranes. The standard deviation of the 25 values measured on these dialyzers was determined to be 0.7 mbar, with the lowest value being 18.7 mbar and the highest value being 21.4 mbar.

In contrast thereto, the 10 pieces of dialyzers having defective membranes showed a significantly increased pressure drop in the range of from 30.0 mbar up to 62.4 mbar.

Example 2

It is important that the amount of water used to wet the pores of the hollow fiber membrane is sufficient to substantially reduce the gas permeability of the membrane. The minimum amount of water required to reliably wet the membrane can be calculated using the equation $P \cdot n \cdot L \cdot \pi \cdot (d_i \cdot 20 \text{ }\mu m + 400 \text{ }\mu m^2)$ with n being the number of fibers in the filter, L being the fiber length, P being the porosity of the fiber membrane, $d_i$ being the inner diameter of each fiber, and w being the wall thickness of each fiber. For the dialyzer of Example 1, the minimum amount is calculated to be 26.4 ml.

Eight dialyzers of the type used in Example 1 and having intact membranes were each wetted with 30 ml of water. A leak test panel (Type: MPS200, JW Froehlich GmbH) was connected to the outlet of the blood compartment of the dialyzer. The inlet of the blood compartment remained closed and both ports of the dialysate compartment were opened to atmospheric pressure.

A pressure of 1.6 bar was applied to the blood compartment of the dialyzer for 2.5 seconds and the ports of the blood compartment were closed. After a leveling phase of one second, pressure decrease inside the blood compartment was measured for another 10 seconds. Finally, the system was vented for 1.5 seconds. The eight filters showed a mean pressure decrease during the measuring phase of 195 mbar with the minimum value being 187 mbar and the maximum value being 202 mbar.

All eight dialyzers were dried afterwards by applying an airstream of 4 m$^3$ h$^{-1}$ through the blood compartment for one hour. After drying of the filters, the experiment was repeated using 27 ml of water instead of 30 ml. In the leak test, the eight filters this time showed a mean pressure decrease during the measuring phase of 230 mbar with the minimum value being 223 mbar and the maximum value being 239 mbar. The reduced amount of water used to wet the membrane resulted in an increased gas permeability of the membrane.

All eight dialyzers were dried afterwards by applying an airstream of 4 m$^3$ h$^{-1}$ through the blood compartment for one hour. After drying of the filters, the experiment was repeated using 25 ml of water instead of 30 ml. For three out of eight dialyzers, it was not possible to establish a pressure of 1.6 bar inside the blood compartment, because air was still able to permeate through the membrane without significant resistance. Thus, 25 ml of water were not sufficient to reliably reduce the gas permeability of this specific membrane.

The invention claimed is:

1. A process for testing a filter comprising two compartments separated by a porous membrane which is a bundle of hollow fiber membranes, comprising
    i) providing a filter having a dry porous membrane which is a bundle of hollow fiber membranes;
    ii) establishing a pressure gradient between the compartments;
    iii) introducing a volume of testing liquid which is sufficient to substantially reduce gas permeability of the porous membrane but is less than or equal to the total pore volume of the porous membrane into the compartment having the higher pressure and permitting the testing liquid to wet the porous membrane;
    iv) monitoring the pressure gradient between the compartments or measuring gas flow through the membrane.

2. The process of claim 1, wherein the testing liquid is water, methanol, ethanol or a mixture thereof.

3. The process of claim 2, wherein the testing liquid is water.

4. The process of claim 1, wherein the testing liquid is isopropanol.

5. The process of claim 1, wherein the testing liquid is at least one of a liquid hydrocarbon and a silicone oil.

6. A device for testing a filter comprising two compartments separated by a porous membrane which is a bundle of hollow fiber membranes, comprising
   i) means for establishing a pressure gradient between the compartments;
   ii) means for introducing a volume of testing liquid into the filter, the volume of testing liquid being sufficient to substantially reduce gas permeability of the porous membrane but less than or equal to the total pore volume of the porous membrane, into the compartment having the higher pressure and allowing the testing liquid to wet the porous membrane;
   iii) means for monitoring the pressure gradient between the compartments or measuring gas flow through the membrane.

7. The device of claim 6, wherein the means for introducing a predefined volume of testing liquid into the filter comprises a dosage compartment having an interruptible fluid connection to a testing liquid reservoir, an interruptible fluid connection to one of the two compartments of the filter, and a vent pipe comprising a valve.

8. The device of claim 7, wherein the dosage compartment is interchangeable with another dosage compartment accommodating a different volume of testing liquid.

9. The device of claim 7, wherein the means for introducing a predefined quantity of testing liquid into the filter comprises a movable lid between the dosage compartment and the testing liquid reservoir.

10. The device of claim 8 wherein the means for introducing a predefined quantity of testing liquid into the filter comprises a movable lid between the dosage compartment and the testing liquid reservoir.

11. The process according to claim 1 wherein the volume of testing liquid is in the range of from $P \cdot n \cdot L \cdot \pi \cdot (d_i \cdot 20 \, \mu m + 400 \, \mu m^2)$ to $P \cdot n \cdot L \cdot \pi \cdot (d_i \cdot w + w^2)$,
   with
   n being the number of fibers in the filter,
   L being the fiber length,
   P being the porosity of the fiber,
   $d_i$ being the inner diameter of each fiber, and
   w being the wall thickness of each fiber.

12. The device according to claim 6 wherein the volume of testing liquid is in the range of from $P \cdot n \cdot L \cdot \pi \cdot (d_i \cdot 20 \, \mu m + 400 \, \mu m^2)$ to $P \cdot n \cdot L \cdot \pi \cdot (d_i \cdot w + w^2)$, with
   n being the number of fibers in the filter,
   L being the fiber length,
   P being the porosity of the fiber,
   $d_i$ being the inner diameter of each fiber, and
   w being the wall thickness of each fiber.

13. A device for testing a filter comprising two compartments separated by a porous membrane which is a bundle of hollow fiber membranes, comprising
   i) means for establishing a pressure gradient between the compartments;
   ii) means, comprising a dosage compartment having an interruptible fluid connection to a testing liquid reservoir, an interruptible fluid connection to one of the two compartments of the filter, and a vent pipe comprising a valve, for introducing a volume of testing liquid into the filter, the volume of testing liquid being in the range of from $P \cdot n \cdot L \cdot \pi \cdot (d_i \cdot 20 \, \mu m + 400 \, \mu m^2)$ to $P \cdot n \cdot L \cdot \pi \cdot (d_i \cdot w + w^2)$, with
   n being the number of fibers in the filter,
   L being the fiber length,
   P being the porosity of the fiber,
   $d_i$ being the inner diameter of each fiber, and
   w being the wall thickness of each fiber; and,
   iii) means for monitoring pressure in the filter.

14. The device of claim 13 wherein the dosage compartment is interchangeable with another dosage compartment accommodating a different volume of testing liquid.

15. The device of claim 13 wherein the means for introducing a predefined quantity of testing liquid into the filter comprises a movable lid between the dosage compartment and the testing liquid reservoir.

16. The device of claim 13 wherein the means for introducing a predefined quantity of testing liquid into the filter comprises a movable lid between the dosage compartment and the testing liquid reservoir.

* * * * *